(12) United States Patent
Jian et al.

(10) Patent No.: US 11,139,069 B2
(45) Date of Patent: Oct. 5, 2021

(54) MEDICAL IMAGE DIAGNOSTIC APPARATUS, IMAGE PROCESSING APPARATUS, AND REGISTRATION METHOD

(71) Applicant: Canon Medical Systems Corporation, Otawara (JP)

(72) Inventors: Weijian Jian, Beijing (CN); Zhe Tang, Beijing (CN); Qi Chen, Beijing (CN); Yu Chen, Beijing (CN)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 132 days.

(21) Appl. No.: 16/451,802

(22) Filed: Jun. 25, 2019

(65) Prior Publication Data

US 2019/0392945 A1  Dec. 26, 2019

(30) Foreign Application Priority Data

Jun. 26, 2018 (CN) .......................... 201810670240.0
May 20, 2019 (JP) ............................ JP2019-094382

(51) Int. Cl.
*G16H 30/40* (2018.01)
*G06K 9/62* (2006.01)
(Continued)

(52) U.S. Cl.
CPC .............. *G16H 30/40* (2018.01); *A61B 5/055* (2013.01); *A61B 6/504* (2013.01); *A61B 6/5247* (2013.01); *A61B 8/0891* (2013.01); *A61B 8/5261* (2013.01); *G06K 9/6232* (2013.01); *G06K 9/6253* (2013.01); *G06T 3/0068* (2013.01); *G06T 7/0014* (2013.01);
(Continued)

(58) Field of Classification Search
CPC .... G16H 30/40; G06K 9/6232; G06K 9/6253; G06K 9/6262; G06T 3/0068; G06T 7/0014; G06T 11/008; G06T 2207/10088; G06T 2207/30101; G06T 2207/10081; G06T 7/337; A61B 6/504; A61B 6/5247; A61B 8/0891; A61B 8/5261; A61B 5/055
USPC ......................................................... 382/131
See application file for complete search history.

(56) References Cited

U.S. PATENT DOCUMENTS 7,983,463 B2 * 7/2011 Sirohey ................. G06T 11/008
382/131
8,213,700 B2 * 7/2012 Periaswamy ............ G06K 9/00
382/131

(Continued)

FOREIGN PATENT DOCUMENTS

| JP | 2007-260396 | 10/2007 |
|---|---|---|
| JP | 2014-134517 | 7/2014 |

(Continued)

*Primary Examiner* — Juan A Torres
(74) *Attorney, Agent, or Firm* — Oblon, McClelland, Maier & Neustadt, L.L.P.

(57) ABSTRACT

A medical image diagnostic apparatus according to an embodiment includes processing circuitry configured to determine a plurality of small blocks for each of a plurality of pieces of medical image data, generate a plurality of superpixels corresponding to the plurality of small blocks, assign a label to at least one of the plurality of pieces of medical image data, and perform registration between the plurality of pieces of medical image data using the plurality of superpixels and the label.

11 Claims, 11 Drawing Sheets

(51) Int. Cl.
*G06T 3/00* (2006.01)
*G06T 7/00* (2017.01)
*G06T 11/00* (2006.01)
*A61B 6/00* (2006.01)
*A61B 8/08* (2006.01)
*A61B 5/055* (2006.01)

(52) U.S. Cl.
CPC .. G06T 11/008 (2013.01); *G06T 2207/10088* (2013.01); *G06T 2207/30101* (2013.01)

(56) References Cited

U.S. PATENT DOCUMENTS

| | | |
|---|---|---|
| 9,389,311 B1 * | 7/2016 | Moya ................ G06K 9/0063 |
| 2006/0215896 A1 | 9/2006 | Sirohey et al. |
| 2015/0131880 A1 | 5/2015 | Wang et al. |
| 2016/0117797 A1 | 4/2016 | Li et al. |
| 2016/0253803 A1 | 9/2016 | Miyamoto et al. |

FOREIGN PATENT DOCUMENTS

| | | |
|---|---|---|
| JP | 2015-93131 | 5/2015 |
| JP | 2015-96196 | 5/2015 |
| WO | WO 2014/196069 A1 | 12/2014 |

\* cited by examiner

MEDICAL IMAGE DIAGNOSTIC APPARATUS, IMAGE PROCESSING APPARATUS, AND REGISTRATION METHOD

CROSS-REFERENCE TO RELATED APPLICATIONS

This application is based upon and claims the benefit of priority from Chinese Patent Application No. 201810670240.0, filed on Jun. 26, 2018; and Japanese Patent Application No. 2019-94382, filed on May 20, 2019, the entire contents of all of which are incorporated herein by reference.

FIELD

Embodiments described herein relate generally to a medical image diagnostic apparatus, an image processing apparatus, and a registration method.

BACKGROUND

For a single image obtained by scanning with a device such as a CT, an MR, or an ultrasonic scanner, in conventional medical image diagnostic apparatuses, there is a technique of obtaining an image of the entire blood vessel portion by manually labeling a tubular tissue such as a blood vessel.

However, for the same patient, when scanned with different devices, for example, when both CT scan and ultrasound scan are performed, for the same tissue, for example, the same blood vessel, sometimes there is the need of comparing its features in images of different modalities (i.e., in CT scan image and in ultrasonic scan image), so as to find a lesion or the like of the blood vessel. However, sometimes since there are many blood vessels in the image, it is difficult for the user to find the corresponding blood vessels in the above mentioned two scanned images, making it impossible to perform a rapid and accurate diagnosis.

DETAILED DESCRIPTION

A medical image diagnostic apparatus comprises processing circuitry. The processing circuitry is configured to determine a plurality of small blocks for each of a plurality of pieces of medical image data, and generate a plurality of superpixels corresponding to the plurality of small blocks; assign a label to at least one of the plurality of pieces of medical image data; and perform registration between the plurality of pieces of medical image data, using the plurality of superpixels and the label.

In the following, embodiments of the medical image diagnostic apparatus, an image processing apparatus, and a registration method thereof will be described with reference to the accompanying drawings.

In the following, a medical image diagnostic apparatus according to a first embodiment will be described with reference to FIG. 1 to FIG. 7E.

Figure 1:
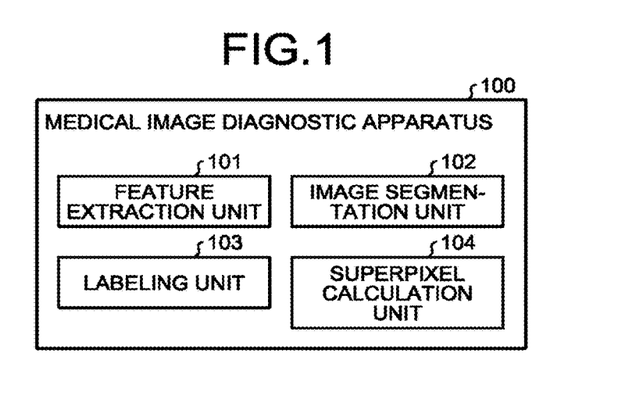
FIG. 1 is a block diagram of the structure of a medical image diagnostic apparatus according to a first embodiment.

FIG. 1 is a block diagram of the structure of a medical image diagnostic apparatus 100.

As shown in FIG. 1, the medical image diagnostic apparatus 100 includes a feature extraction unit 101, an image segmentation unit 102, a labeling unit 103, and a superpixel calculation unit 104. The image segmentation unit 102 is one example of a generating unit. The labeling unit 103 is one example of a labeling unit. The superpixel calculation unit 104 is one example of a registration unit.

The feature extraction unit 101, the image segmentation unit 102, the labeling unit 103, and the superpixel calculation unit 104 may be implemented by the processing circuitry. The processing circuitry is processor that implements the functions that correspond to the respective programs by reading the programs from memory and executing them.

The feature extraction unit 101 extracts image features such as grayscale value, gradient, shape, position, and Hessian matrix for a medical image selected by a user such as a doctor.

The image segmentation unit 102 is used for performing superpixel segmentation on medical images selected by the user.

Superpixel segmentation is a process of subdividing an image into multiple image sub-regions, i.e., superpixels, in order to locate objects and boundaries, etc. in the image. A superpixel is a small region consists of a series of pixels whose positions are adjacent and whose characteristics (such as color, brightness, and texture) are similar.

Figure 2A:
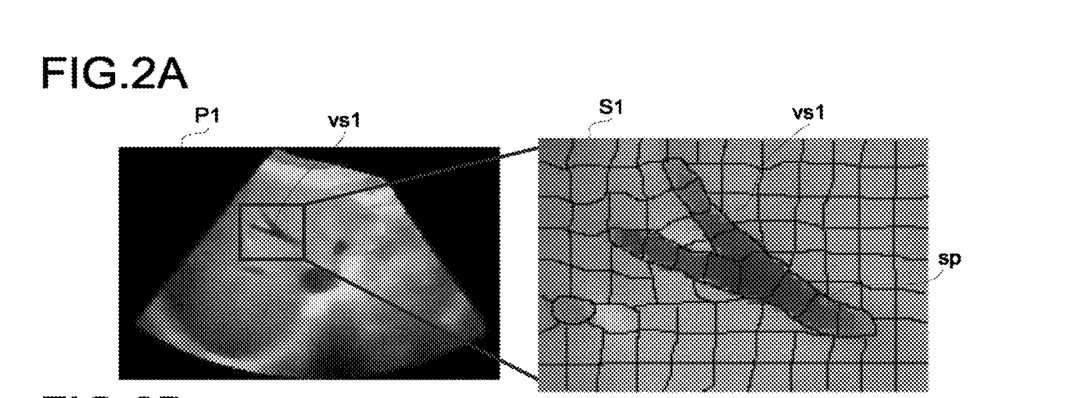
FIG. 2A is a schematic view of a superpixel segmentation performed on a medical image.
Figure 2B:
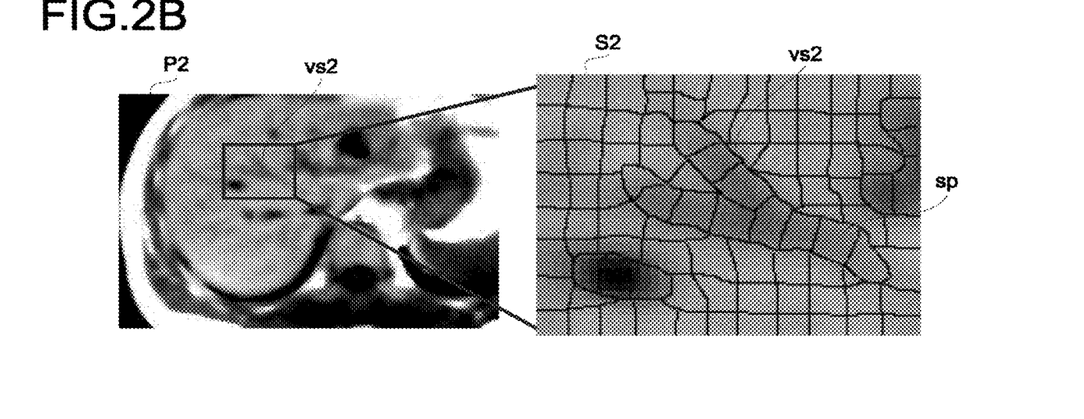
FIG. 2B is a schematic view of a superpixel segmentation performed on a medical image.

FIG. 2A and FIG. 2B are two images taken on the same patient, wherein the left side image of FIG. 2A is an ultrasound image P1, and the left side image of FIG. 2B is a CT image P2, in both images, the same vessels are shown respectively, a blood vessel vs1 is shown in the ultrasonic image P1, and a blood vessel vs2 which is the same as the blood vessel vs1 is shown in the CT image P2. A blood vessel is one example of a tubular structure.

The graph on the right side of FIG. 2A is a superpixel segmentation map S1 including the blood vessel vs1, which is an enlarged view of the box part in the image after a superpixel segmentation of the ultrasound image P1, and the graph on the right side of FIG. 2B is a superpixel segmentation map S2 including the blood vessel vs2, which is an enlarged view of the box part in the image after a superpixel segmentation of the CT image P2. The superpixel segmentation map S1 and the superpixel segmentation map S2 are each composed of a plurality of superpixels sp.

In FIG. 2A, only the Y-shaped blood vessel including the blood vessel vs1 is clearly shown, and in FIG. 2B, the Y-shaped blood vessel including the blood vessel vs2 is clearly shown, however, the figures are chosen for the convenience of the description, and generally, a plurality of blood vessels will present in each image, in case the blood vessel vs1 is located in the ultrasound image P1, it would be difficult to find the corresponding same blood vessel vs2 in the CT image P2 with naked eye.

Further, in the present embodiment, the ultrasonic image P1 is used to represent the reference image, and the CT image P2 is used to represent the floating image. By continuously labeling the superpixels constituting the blood vessel on the ultrasonic image P1 representative of the reference image, it is possible to automatically display the superpixels of the corresponding vessel on the CT image P2 representative of the floating image, thereby displaying the corresponding blood vessel.

The labeling unit 103 receives a labeling applied by a user with a finger or an electronic pen or the like on a superpixel segmentation map displayed on the touch panel, i.e., label assignment, and can highlight the superpixels where the labeled point resides or the superpixels the labeled line passes, that is, a plurality of superpixels corresponding to a plurality of small blocks determined within each medical image data can be generated based on the assigned labels. The highlighting may be distinguished from other superpixels by, for example, changing the color of the superpixel or the like.

For the same component, such as the vessel in the reference image and the floating image, the superpixel calculation unit 104 calculates the superpixels on the floating image that correspond to the superpixels on the reference image in accordance with the plurality of superpixels highlighted by continuous line labeling on the reference image and the starting superpixel labeled on the floating image, and highlights it, thereby performing registration between the pieces of data of the reference image and the floating image.

Figure 3:
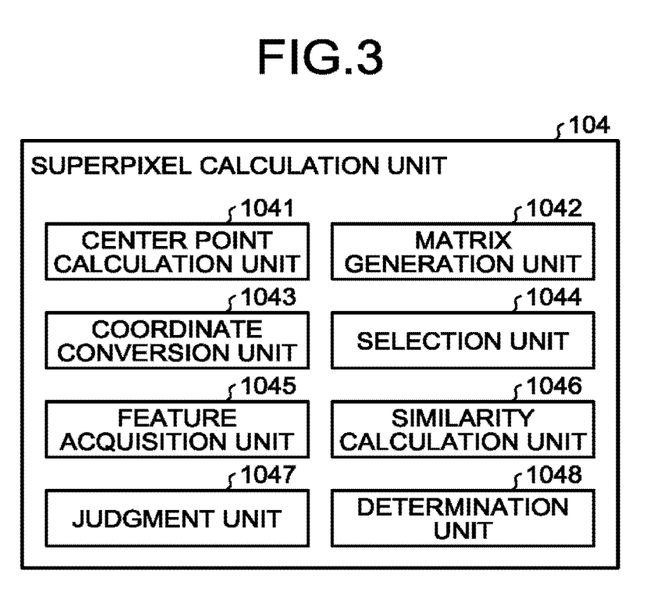
FIG. 3 is a structural diagram of a superpixel calculation unit.

FIG. 3 is a structure diagram showing the structure of the superpixel calculation unit 104. The superpixel calculation unit 104 comprises a center point calculation unit 1041, a matrix generation unit 1042, a coordinate conversion unit 1043, a selection unit 1044, a feature acquisition unit 1045, a similarity calculation unit 1046, a judgment unit 1047, and a determination unit 1048.

The center point calculation unit 1041 can calculate the centroid of the superpixel as the center point of the superpixel for the superpixel highlighted by the labeling unit 103.

Figure 4A:
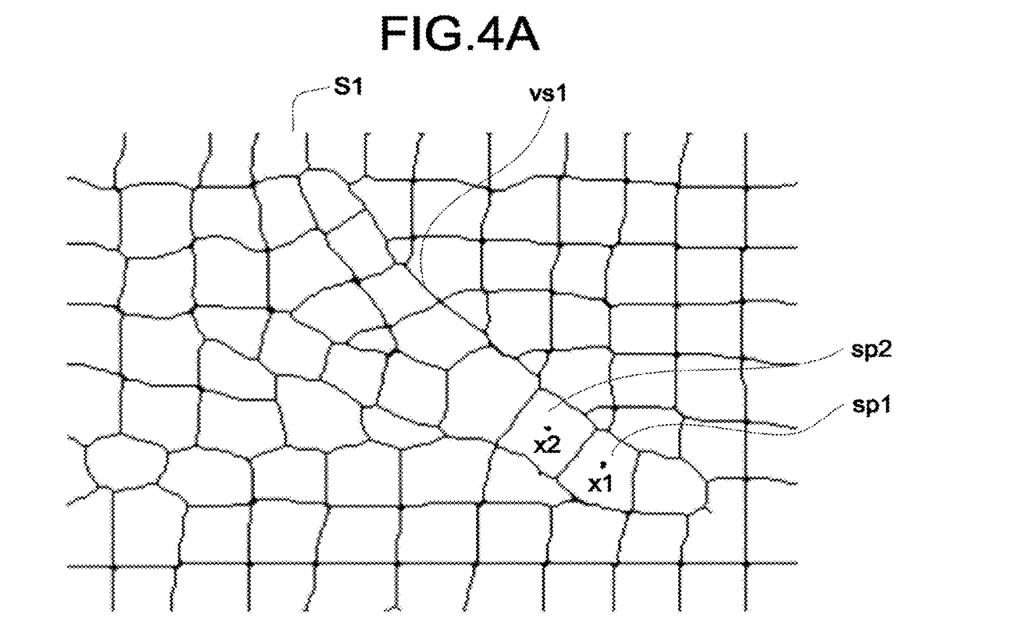
FIG. 4A is a graph for illustrating registration processing between pieces of medical image data.
Figure 4B:
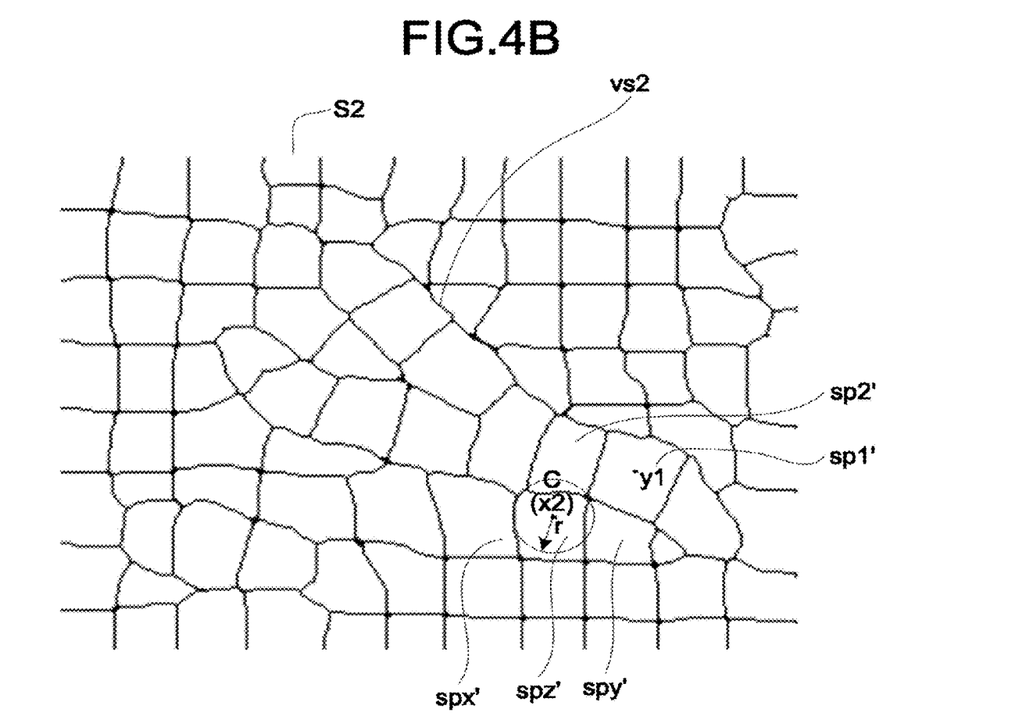
FIG. 4B is a graph for illustrating registration processing between pieces of medical image data.

FIG. 4A and FIG. 4B are diagrams for illustrating registration processing between pieces of medical image data, in which FIG. 4A corresponds to the superpixel segmentation map S1 in FIG. 2A, and FIG. 4B corresponds to the superpixel segmentation map S2 in FIG. 2B. In FIG. 4A and FIG. 4B, in order to make each label clearer, the grayscale in the superpixel segmentation maps S1 and S2 are removed.

As shown in FIG. 4A and FIG. 4B, in the superpixel segmentation map S1, the center point calculation unit 1041 can calculate the center points of the superpixel sp1 and the superpixel sp2 obtained by labeling, and the center points are represented by coordinates x1 and x2, respectively. In the superpixel segmentation map S2, the center point calculation unit 1041 can calculate the center point of the superpixel sp1' obtained by labeling, and the center point is represented by the coordinate y1.

The matrix generation unit 1042 generates a transformation matrix T between the blood vessel vs1 of the superpixel segmentation map S1 and the blood vessel vs2 of the superpixel segmentation map S2 in accordance with the coordinates of the center points of the plurality of superpixels (at least two superpixels) of the blood vessel vs1 of the superpixel segmentation map S1 and the coordinates of the center points of the superpixels of the blood vessel vs2 of the segmentation map S2 corresponding to the plurality of superpixels of blood vessel vs1. The transformation matrix T is, for example, an affine transformation matrix, which can be calculated, for example, by a least squares method.

The coordinate conversion unit 1043 multiplies the coordinate x2 with the transformation matrix T to obtain the predicted coordinate C (x2) of the superpixel sp2' of the superpixel segmentation map S2.

The selection unit 1044 selects superpixels located completely or partly within the range of a region with a radius r centered on the coordinate C (x2) respectively, as shown in FIG. 4A and FIG. 4B, the superpixels spx', spy', spz', sp2' are selected, respectively. Of course, the scale of the radius r can be set as needed.

The feature acquisition unit 1045 acquires the respective features (such as grayscale value, gradient, shape, location, and Hessian matrix, etc.) of the features extracted from the feature extraction unit 101 for each of the superpixels spx', spy', spz', sp2'.

For example, 1-d features of the superpixels are obtained, when obtaining the features of superpixel spx', the features are represented by a set $a_j=(a_{j1}, a_{j2}, \ldots, a_{jd})$. Meanwhile, for the superpixel sp2 in the superpixel segmentation map S1, the feature acquisition unit 1045 obtains its feature $a_2=(a_{21}, a_{22}, \ldots, a_{2d})$.

The similarity calculation unit 1046 calculates the similarity of the features between the superpixel sp2 in the superpixel segmentation map S1 and the superpixel spx' in the superpixel segmentation map S2, specifically, puts the features $a_j$ and $a_2$ into one set, i.e., forming a set $ak=(a_2, a_j)=(a_{21}, a_{22}, \ldots, a_{2d}, a_{j1}, a_{j2}, \ldots, a_{jd})$, and compares each feature, to calculate the similarity $s_{2j}$ of the overall feature $a_j$ and $a_2$.

The judgment unit 1047 judges whether or not all superpixels within the range of the radius r centered on the coordinate C (x2) in the superpixel segmentation map S2 of the CT image P2 are selected.

By comparing the feature of each of the superpixels spx', spy', spz', and sp2' with the feature of the superpixel sp2, the determination unit 1048 determines the superpixel having the closest similarity (the highest similarity) as the superpixel in the CT image P2 that corresponds to the superpixel sp2.

Figure 5:
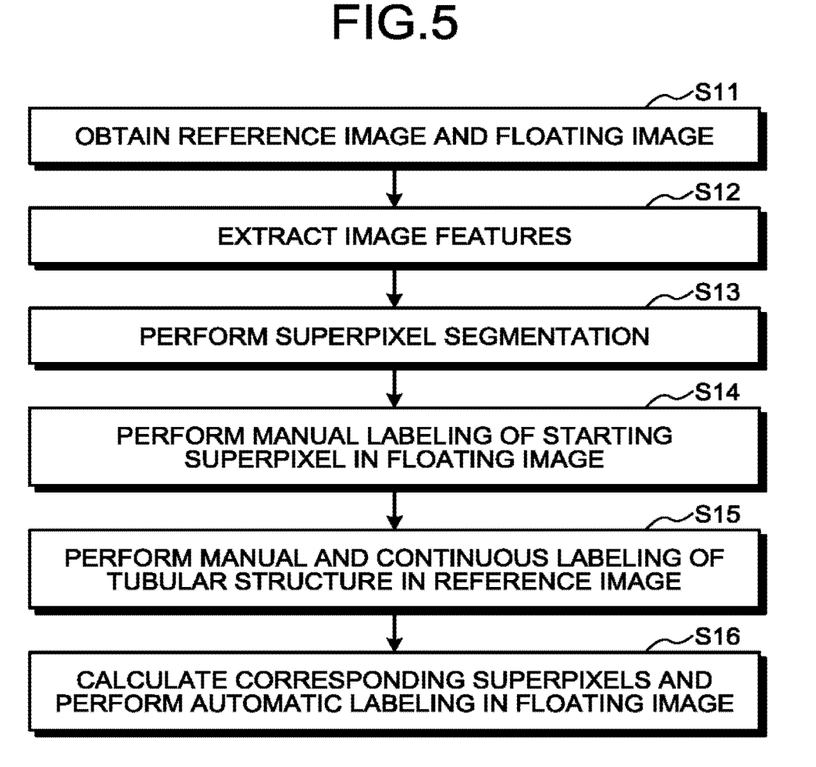
FIG. 5 is a flowchart for illustrating registration processing between pieces of medical image data.

In the following, the registration processing of the medical image data will be described based on FIG. 2A and FIG. 2B, FIG. 4A and FIG. 4B, and FIG. 5, wherein FIG. 5 is a flowchart for illustrating the registration processing of the medical image data.

First, the user finds two images taken on the same patient, i.e., an ultrasound image P1 (reference image) and a CT image P2 (floating image). And in the two images, the user judges that the same blood vessel (i.e., the blood vessel vs1 in the ultrasound image P1 and the blood vessel vs2 in the CT image P2) should exist by a comparison of image slice position. That is, the user obtains the reference image and the floating image in which the same blood vessel exists (step S11).

After that, the feature extraction unit 101 extracts image features such as grayscale value, gradient, shape, position, and Hessian matrix for the ultrasound image P1 and the CT image P2 (step S12).

After that, as shown in the superpixel segmentation map S1 and the superpixel segmentation map S2 in the right portion of FIG. 2A and FIG. 2B, the image segmentation unit 102 performs superpixel segmentation on the ultrasound image P1 and the CT image P2 selected by the user (step S13).

After that, as shown in FIG. 4B, in the superpixel segmentation map S2, that is, in the CT image P2, the user performs manual labeling by touching the position of the superpixel sp1' with a finger or an electronic pen or the like, and the labeling unit 103 receives the user's labeling, i.e., label assignment, thereby highlighting the superpixel sp1' where the labeled point resides, that is, generating the superpixel sp1' (step S14).

After that, as shown in FIG. 4A, in the superpixel segmentation map S1, that is, in the ultrasound image P1, using a finger or an electronic pen or the like, along the extending direction of the blood vessel vs1, taking the position of the superpixel sp1 that corresponds to the superpixel sp1' as the starting point, the user draws a line continuously, thereby manually labeling the blood vessel vs1. The labeling unit 103 receives the user's labeling, that is, label assignment, thereby highlighting the superpixels sp1, sp2, etc. where the labeled line is located, and the blood vessel vs1 is gradually displayed (step S15).

After that, in the superpixel segmentation map S2 (i.e., the CT image P2), the superpixel calculating unit 104 calculates superpixels corresponding to the plurality of superpixels of the ultrasound image P1 in accordance with the plurality of superpixels highlighted by labeling by the continuous drawing a line on the superpixel segmentation map S1 (i.e., the ultrasonic image P1) and the starting pixel labeled on the superpixel segmentation map S2 (i.e., the CT image P2), and automatically labeling is performed by highlighting (step S16).

Figure 6:
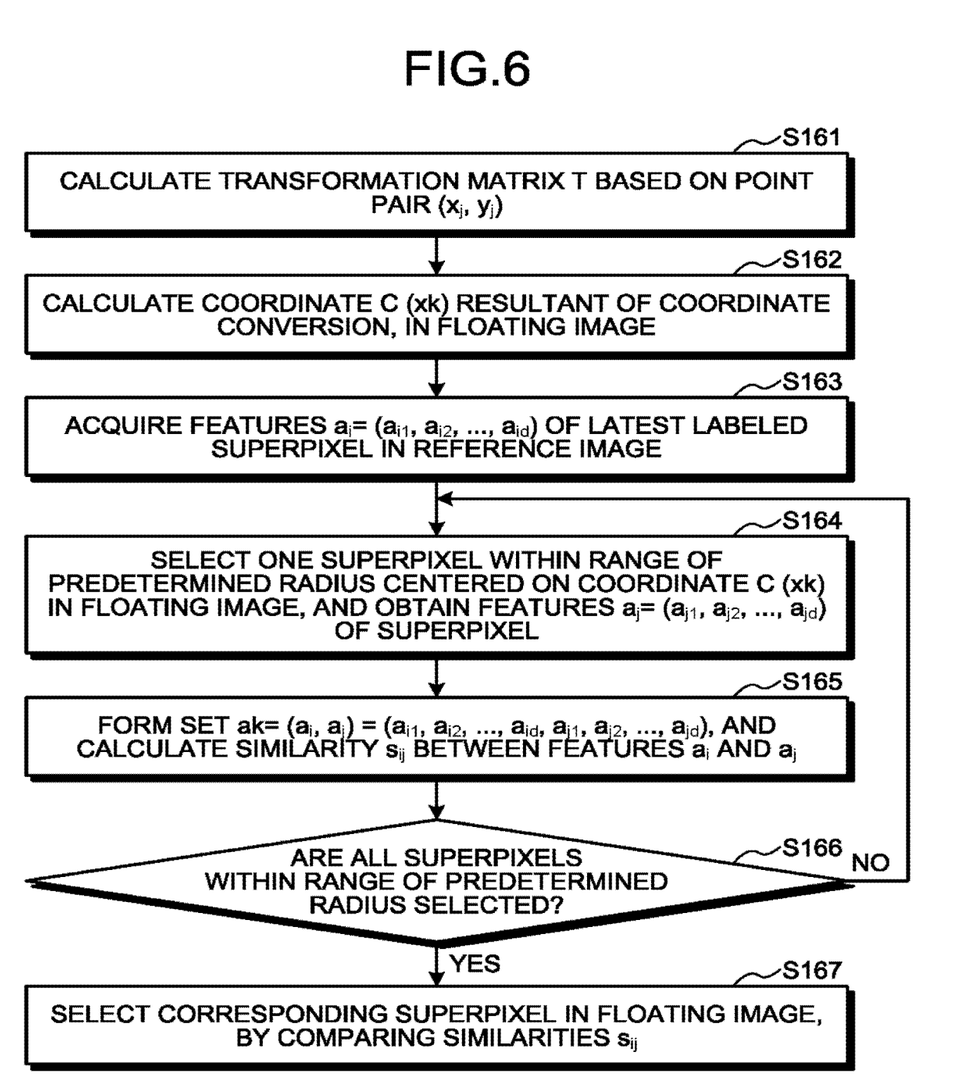
FIG. 6 is a flowchart for illustrating how to find a corresponding superpixel in a floating image.

In the following, a method of calculating corresponding superpixels in the CT image P2 will be described based on FIG. 4A, FIG. 4B, and FIG. 6, wherein FIG. 6 is a flowchart for illustrating how to find a corresponding superpixel in a floating image.

First, as shown in FIG. 4A, for the superpixel segmentation map S1, the center point calculation unit 1041 calculates the superpixel sp2 labeled by the continuous drawing the line and the coordinates the center points x1 and x2 of the superpixel sp1. For the superpixel segmentation map S2, the center point calculation unit 1041 calculates the center point coordinate y1 of the superpixel sp1' obtained by the labeling. And the matrix generation unit 1042 generates transformation matrix T between the blood vessel vs1 of the superpixel segmentation map S1 and the blood vessels vs2 of the superpixel segmentation map S2 in accordance with the coordinates of the center points x1, x2, and y1 (step S161).

After that, as shown in FIG. 4B, in the superpixel segmentation map S2 (i.e., the CT image P2), the coordinate conversion unit 1043 multiplies the coordinate x2 with the transformation matrix T to obtain the predicted coordinate C(x2) of the superpixel sp2' of the superpixel segmentation map S2 (step S162).

After that, as shown in FIG. 4A, in the superpixel segmentation map S1 (i.e., the ultrasound image P1), the feature acquisition unit 1045 acquires the features of the later labeled (i.e., the newest labeled) superpixel sp2 in the line labeling, $a_2=(a_{21}, a_{22}, \ldots, a_{2d})$ (step S163).

After that, as shown in FIG. 4B, in the superpixel segmentation map S2 (i.e., the CT image P2), within the range of the radius r centered on the coordinate C (x2), the selection unit 1044 selects the superpixels that are partly within the range. For the superpixel spx', the feature acquisition unit 1045 obtains the feature $a_j=(a_{j1}, a_{j2}, \ldots, a_{jd})$ from the feature extracted by the feature extraction unit 101 (step S164).

After that, the similarity calculation unit 1046 puts the features $a_j$ and $a_2$ into one set, that is, forming the set $ak=(a_2, a_j)=(a_{21}, a_{22}, \ldots, a_{2d}, a_{j1}, a_{j2}, \ldots, a_{jd})$, and compares each feature to calculate the similarity $s_{2j}$ of the whole $a_2$ and $a_j$, thereby calculating a similarity between the features of the superpixel sp2 in the superpixel segmentation map S1 and the superpixel spx' in the superpixel segmentation map S2 (step S165).

After that, the judgment unit 1047 judges whether all superpixels within the range of the radius r centered on the coordinate C (x2) are selected (step S166). In case it is judged that not all the superpixels are selected (NO in step S166), the method returns to step S164, and as shown in FIG. 4B, in the superpixel segmentation map S2, superpixel spy', spz' or sp2' are selected and their features are obtained, and then proceeding to step S165. In case it is determined superpixels spx', spy', spz', sp2' are all selected (YES in step S166), by comparing the similarity of the features of each of the superpixels spx', spy', spz', sp2' with the features of the superpixel sp2, the determination unit 1048 determines the superpixel having closest similarity as the corresponding superpixel in the CT image P2 (step S167). Here, since the grayscale of superpixel sp2' is most similar to that of superpixel sp2, both are blood vessels, and the shapes are also similar and so on, therefore, in the CT image P2, the superpixel sp2' is determined as the superpixel that corresponds to the superpixel sp2 in the ultrasonic image P1.

Figure 7A:
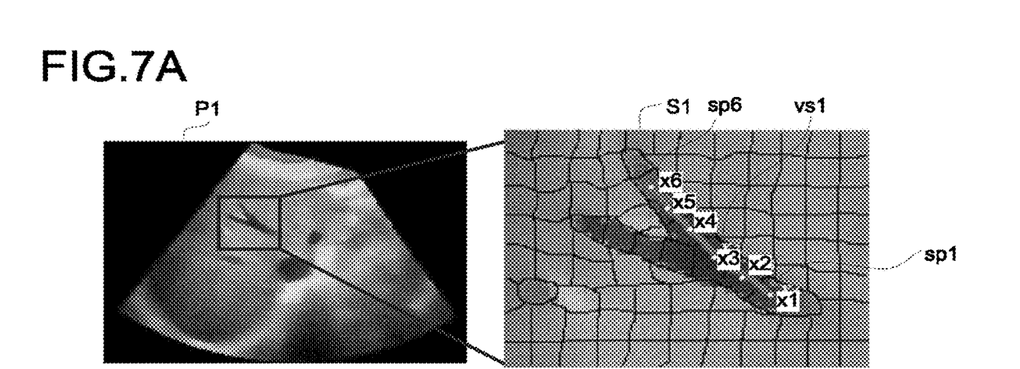
FIG. 7A is a schematic diagram showing a state in which medical image data has been registered.
Figure 7B:
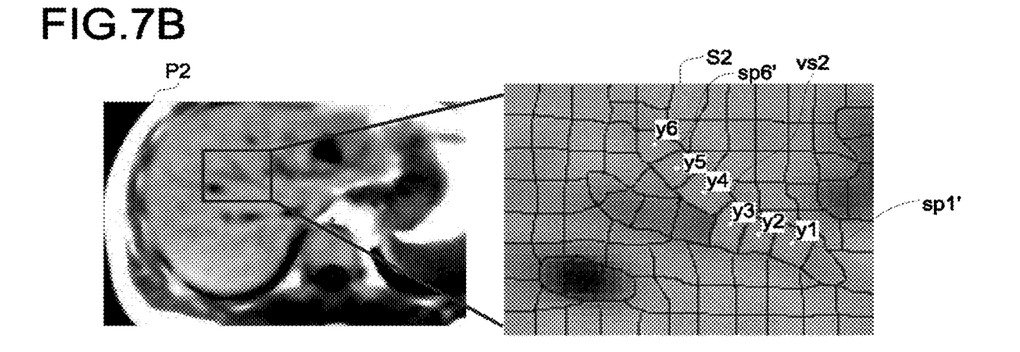
FIG. 7B is a schematic diagram showing a state in which medical image data has been registered.

FIG. 7A and FIG. 7B are diagrams showing a state in which medical image data has been registered. In FIG. 7B, in the superpixel segmentation map S2 in the CT image P2, in case a certain point of the region where the superpixel sp1' (starting superpixel) resides is labeled, in FIG. 7A, in the superpixel segmentation map S1 in the ultrasound image P1, when a line is continuously drawn from a certain point of the region where the superpixel sp1 (starting superpixel) resides to a certain superpixel in the region where the superpixel sp6 resides along the direction of the blood vessel vs1, as is shown in FIG. 7B, it can be automatically labeled to the superpixel sp6' in the superpixel segmentation map S2 in the CT image P2, thereby automatically finding the blood vessel vs2 corresponding to blood vessel vs1. Therefore, the user can easily find the same blood vessel in the two scanned images of the ultrasonic image P1 and the CT image P2, thereby enabling rapid and accurate diagnosis.

Further, in the superpixel calculation unit 104, the feature acquisition unit 1045 and the judgment unit 1047 may not be provided, and when the feature acquisition unit 1045 is not provided, the feature extraction unit 101 provides the feature of the superpixel, and when the judgment unit 1047 is not provided, Step S166 in FIG. 6 is omitted, and in this case, in step S164, as shown in FIG. 4B, in the superpixel segmentation map S2 (i.e., the CT image P2), within the range of a radius r centered on the coordinate C (x2), the selection unit 1044 selects all the superpixels spx', spy', spz', and sp2' that are partly within the range. And the features of each superpixel are provided by the feature extraction unit 101. Thereafter, in step S165, the similarity calculation unit 1046 calculates the similarity between the features of the superpixel sp2 in the superpixel segmentation map S1 and the superpixels spx', spy', spz' and sp2' in the superpixel segmentation map S2. After that, at step S167, the determination unit 1048 determines the superpixel in superpixels spx', spy', spz', sp2' with features most similar to the superpixel sp2 as the corresponding superpixel in CT image P2.

In addition, as described above, the method of calculating the corresponding superpixel is illustrated by taking FIG. 4A and FIG. 4B as an example. In FIG. 7A and FIG. 7B, in calculating the superpixel sp6', the transformation matrix T between the blood vessel vs1 and the blood vessel vs2 is calculated in accordance with the coordinates x1, x2, x3, x4, x5 of the center point of respective superpixels of the blood vessel vs1 in the superpixel segmentation S1 and the coordinates y1, y2, y3, y4, y5 of the center point of the superpixel of the blood vessel vs2 in the superpixel segmentation map S2 corresponding to the coordinates of the center points of the above-described respective superpixels. And the predicted coordinate of the center point of the superpixel sp6' is calculated by multiplying the center point coordinate x6 of the superpixel sp6 with the transformation matrix T, and the calculation method of the superpixel sp6' thereafter resembles the steps S163-step S167 in FIG. 6.

In the following, a medical image diagnostic apparatus 200 according to a second embodiment will be described with reference to FIG. 8 to FIG. 10.

Moreover, only the distinguishing parts that differ from the first embodiment will be described, and parts that are the same as those in the first embodiment are given corresponding reference numbers, to avoid repeated description or simplify the description.

Figure 8:
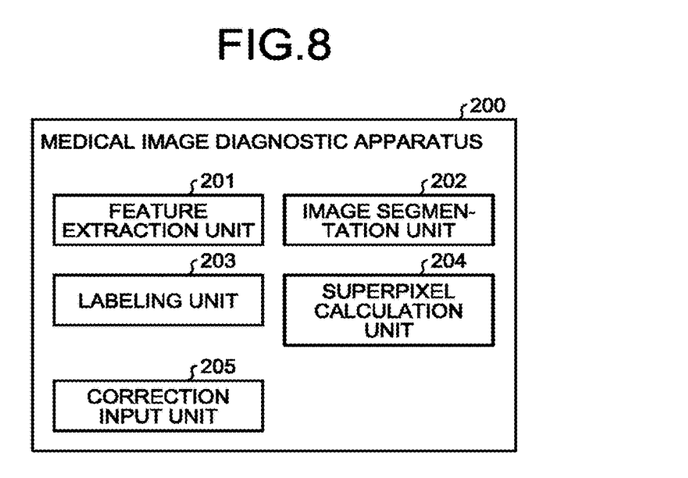
FIG. 8 is a block diagram of the structure of a medical image diagnostic apparatus according to a second embodiment.
Figure 9A:
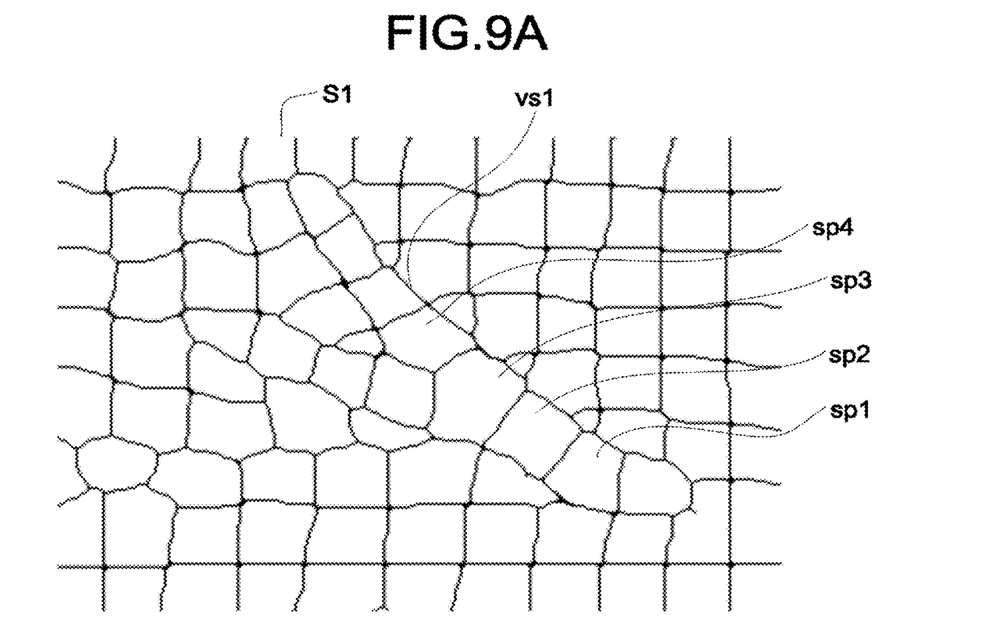
FIG. 9A is a diagram illustrative of the correction made when there is an error in the superpixel calculated in a floating image.
Figure 9B:
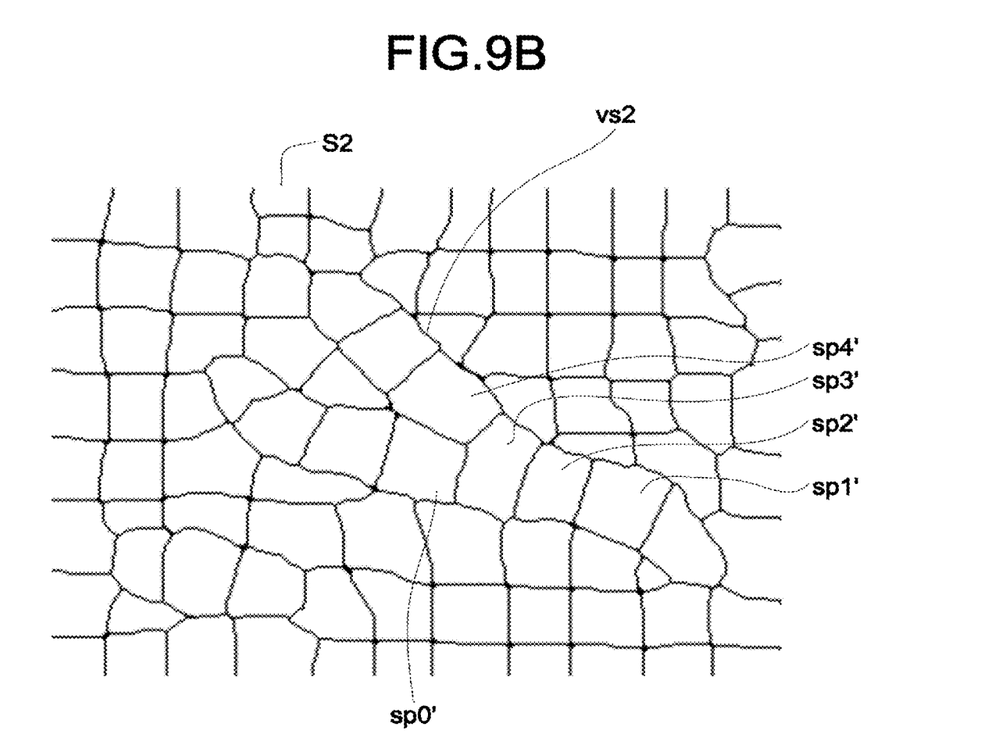
FIG. 9B is a diagram illustrative of the correction made when there is an error in the superpixel calculated in a floating image.
Figure 10:
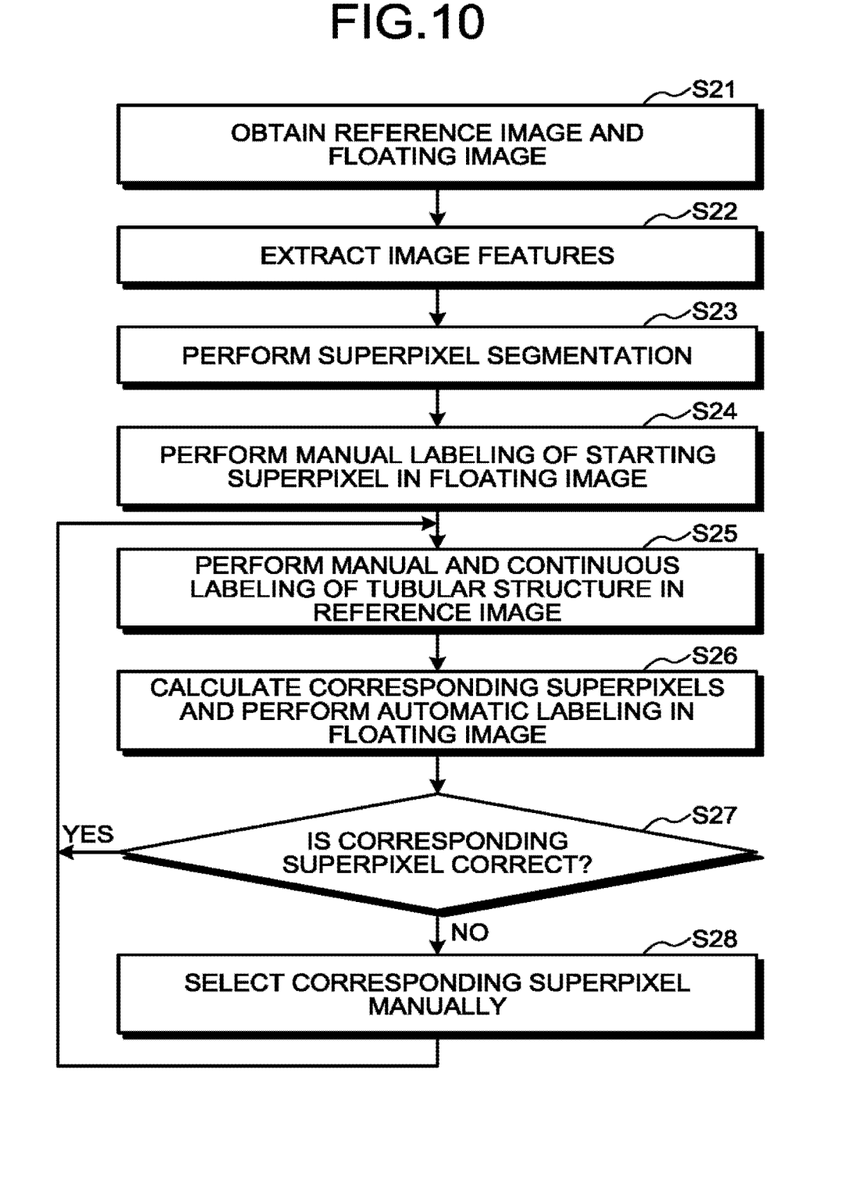
FIG. 10 is a flowchart of the registration processing of medical image data according to a second embodiment.

FIG. 8 is a structure block diagram of the medical image diagnostic apparatus 200, FIG. 9A and FIG. 9B are illustrative diagrams of correcting a superpixel error calculated in the superpixel segmentation map S2 of the CT image, and FIG. 10 is a flowchart of the registration processing of the medical image data.

As shown in FIG. 8, the medical image diagnostic apparatus 200 includes a feature extraction unit 201, an image segmentation unit 202, a labeling unit 203, a superpixel calculation unit 204 and a correction input unit 205.

Wherein the functions of the feature extraction unit 201, the image segmentation unit 202, the labeling unit 203, and the superpixel calculation unit 204 are the same as the feature extraction unit 101, the image segmentation unit 102, the labeling unit 103, and the superpixel calculation unit 104 in the first embodiment, and therefore, a simplified description is made.

The feature extraction unit 201 extracts image features such as grays ale value, gradient, shape, position, and Hessian matrix for a medical image selected by a user such as a doctor.

The image segmentation unit 202 is used for performing superpixel segmentation on medical images selected by the user.

The labeling unit 203 receives a labeling applied by a user with a finger or an electronic pen or the like on a superpixel segmentation map displayed on the touch panel, i.e., label assignment, and can highlight the superpixel where the labeled point resides or the superpixel where the labeled line passes.

In accordance with the plurality of superpixels highlighted by labeling on the reference image by continuous drawing lines, the superpixel calculation unit 204 calculates the corresponding superpixels on the floating image, and highlights them.

In response to the calculation result (registration result) of the superpixel calculation unit 204, the user (operator) judges whether the calculation result is appropriate, and if it is determined to be inappropriate, the correction input unit 205 receives the correction indication made by the user via label assignment.

In the following, the functions of the correction input unit 205 will be described based on FIG. 9A and FIG. 9B.

In FIG. 9B, in the superpixel segmentation map S2 in the CT image, in case a certain point of the region where the superpixel sp1' (starting superpixel) resides is labeled, the superpixel sp1' is generated by the labeling unit 203. And in FIG. 9A, in the superpixel segmentation map S1 in the ultrasound image, when continuously drawing a line from a certain point of the region where the superpixel sp1 (starting superpixel) resides, along the direction of the blood vessel vs1, to the certain point of the region where the superpixel sp4 resides via the superpixels sp2, sp3, for the superpixels sp2, sp3, the superpixel calculation unit 204 calculates in the blood vessel vs2 of the superpixel segmentation map S2 its corresponding superpixel as sp2' and sp3', and for the superpixel sp4, the superpixel calculation unit 204 calculates its corresponding superpixel as sp0'. And at this time instant, the user realizes that the calculation result is inappropriate (i.e., erroneous), he touches the display screen with a finger or an electronic pen or the like to drag the superpixel sp0' to the correct superpixel sp4', or he clicks on the superpixel sp0' first and then clicks on the superpixel sp4' or in some other way to assign a label for correction indication, the correction input unit 205 receives the correction indication from the user.

In the following, the registration processing of medical image data will be illustrated based on FIG. 9A, FIG. 9B, and FIG. 10.

Wherein steps S21 to S26 are the same as steps S11 to S16 of the first embodiment, and thus repeated descriptions will be omitted.

In step S27, if the user judges that the calculation result of the superpixel calculation unit 204 is correct (YES in step S27), the method returns to step S25, the action of continuously manually labeling the blood vessel in the ultrasound image (i.e., the reference image) continues; and if the user judges that the calculation result of the superpixel calculation unit 204 is inappropriate, i.e., if it is erroneous (NO in step S27), the user assigns a label to make the correction indication, and the correction input unit 205 receives the correction indication from the user, and based on the label after the correction indication, the labeling unit 203 generate the superpixel in such a way that it highlights the superpixel in which the label resides. And as is shown in FIG. 9B, the erroneous superpixel sp0' is corrected to the correct superpixel sp4', that is, the corresponding correct superpixel is manually selected (step S28). And after that, the method returns to step S25 to continue the action of continuously manually labeling the blood vessel in the ultrasonic image, i.e., the reference image.

Therefore, in case the calculation result of the superpixel calculation unit 204 is erroneous, the erroneous superpixel can be manually corrected to the correct superpixel, so that the user can easily find in the CT image (i.e., the floating image) the blood vessel vs2 that is the same as the blood vessel vs1 in the ultrasound image (i.e., the reference image), thereby enabling rapid and accurate diagnosis.

In the following, a medical image diagnostic apparatus according to a third embodiment will be described with reference to FIG. 11 to FIG. 12.

Moreover, only the distinguishing parts that differ from the second embodiment will be described, and parts that are the same as those in the second embodiment are given corresponding reference numbers, to omit repeated descriptions.

Figure 11:
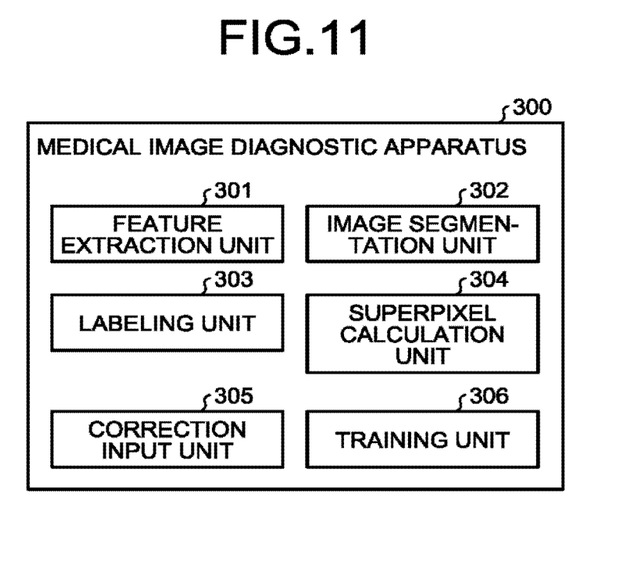
FIG. 11 is a block diagram of the structure of a medical image diagnostic apparatus according to a third embodiment.
Figure 12:
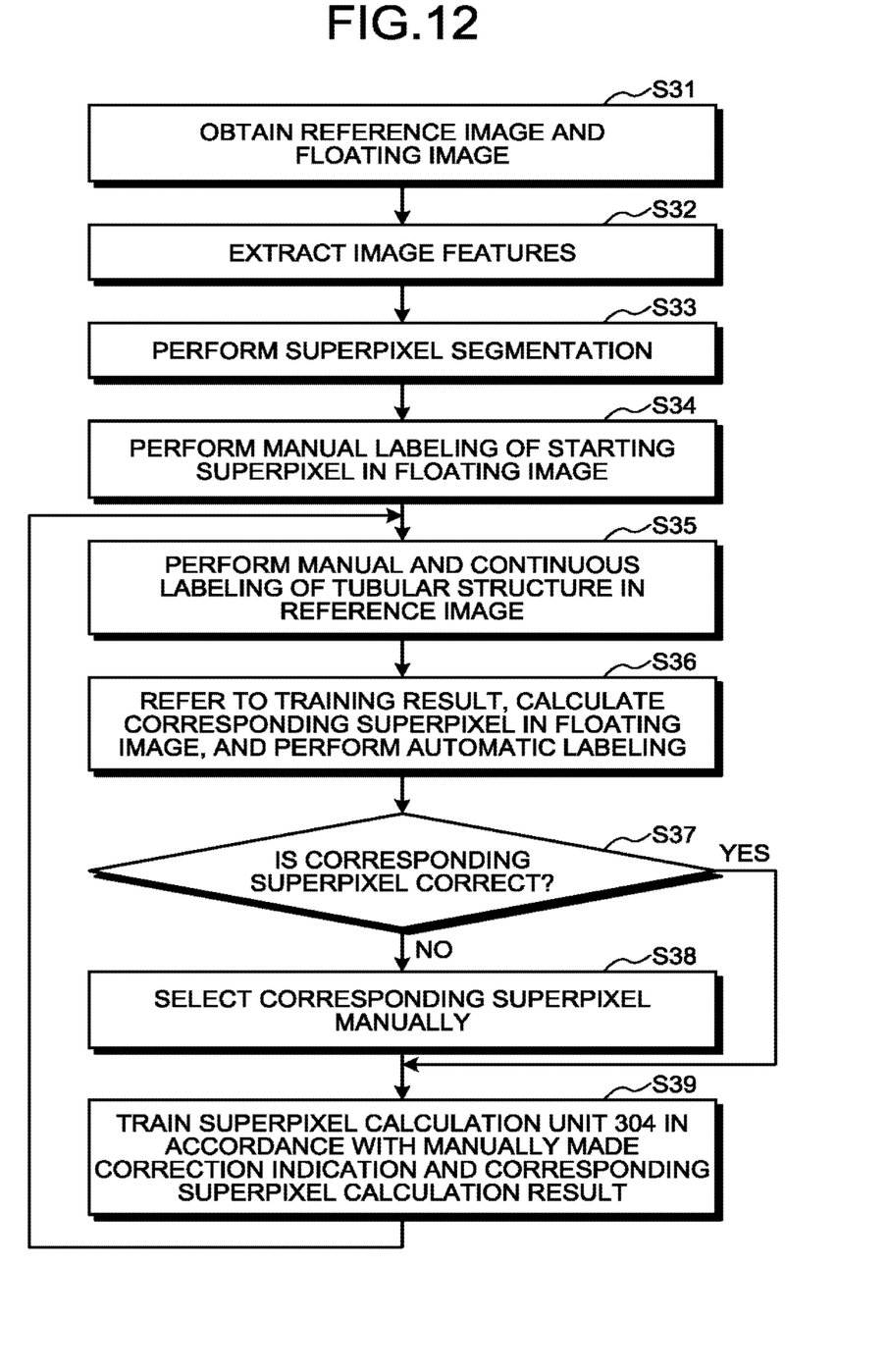
FIG. 12 is a flowchart of the registration processing of medical image data according to a third embodiment.

FIG. 11 is a structure block diagram of a medical image diagnostic apparatus 300 of the third embodiment. FIG. 12 is a flowchart of the registration processing of medical image data.

The medical image diagnostic apparatus 300 includes a feature extraction unit 301, an image segmentation unit 302, a labeling unit 303, a superpixel calculation unit 304, a correction input unit 305 and a training unit 306.

Wherein the functions of the feature extraction unit 301, the image segmentation unit 302, the labeling unit 303, the superpixel calculation unit 304 and the correction input unit 305 are the same as the feature extraction unit 201, the image segmentation unit 202, the labeling unit 203, the superpixel calculation unit 204 and the correction input unit 205 in the second embodiment, and therefore, a simplified description is made.

The training unit 306 trains the superpixel calculation unit 304 in the following way: storing the correction indication received by the correction input unit 305 and the calculation result of the superpixel calculated by the superpixel calculation unit 304, assigning high weights to the correct calculation result of the superpixel, and assigning low weights to the erroneous calculations indicated to be corrected. As the training process is iterated, thereafter, the probability that the correct superpixels are selected gets higher and higher.

In the following, the registration processing of medical image data will be illustrated based on FIG. 12.

Wherein steps S31 to S35, step S37, and step S38 are the same as steps S21 to S25, step S27, and step S28 of the second embodiment, and therefore repeated descriptions will be omitted.

In step S39, the training unit 306 trains the superpixel calculation unit 304 in accordance with the correction indication received by the correction input unit 305 and the calculation result of the correct superpixel calculated by the superpixel calculation unit 304, and the training result is reflected in the later generation of the superpixels, in order to generate the correct superpixels in the subsequent generation of the superpixels.

In step S36, the superpixel calculation unit 304 refers to the previous training result obtained by the training made to the superpixel calculation unit 304 by the training unit 306, and calculates in the CT image (i.e., the floating image) the superpixel corresponding to the superpixel in the ultrasound image (i.e., the reference image), and automatically labels the superpixel.

In the above embodiment, by training the superpixel calculation unit 304 by the training unit 306, the calculation result of the superpixel of the superpixel calculation unit 304 can be made more accurate, so that the user can perform a more rapid and accurate diagnosis.

Moreover, in the above-described embodiment, it can also be constructed as, the superpixel calculation unit 304 is provided with a learning unit that learns the correction indication received by the correction input unit 305 and reflects the learning result in the later generation of the superpixel by the superpixel calculation unit 304 of the medical image diagnostic apparatus 300.

In the above embodiment, an ultrasound image and a CT image are taken as an example to perform registration between their pieces of data. However, images obtained by other imaging modalities are possible. Further, for convenience of explanation, nominations such as reference image and floating image are used, but other nominations can be used as long as they are multiple images taken on the same patient.

The first to the third embodiments are explained above, but, in addition to those embodiments described above, implementations in various different forms are still possible.

For example, explained in the above embodiments is the registration between two images, but the configuration is also applicable to registration between three or more images. In the following, an example of registration between an ultrasound image, a CT image, and an MR image will be explained.

For example, first, the feature extraction unit 101, the feature extraction unit 201, or the feature extraction unit 301 (hereinafter, simply referred to as a feature extraction unit) extracts image features from each of the ultrasound image, the CT image, and the MR image. The image segmentation unit 102, the image segmentation unit 202, or the image segmentation unit 302 (hereinafter, simply referred to as an image segmentation unit) then determines a plurality of small blocks for each of the ultrasound image, the CT image, and the MR image based on the extracted image features, and generates a plurality of superpixels corresponding to the determined plurality of small blocks.

The labeling unit 103, the labeling unit 203, or the labeling unit 303 (hereinafter, simply referred to as a labeling unit) then assigns a label to the medical image data of at least one of the ultrasound image, the CT image, and the MR image. For example, the labeling unit assigns a label to the ultrasound image by receiving an input operation from an operator.

The superpixel calculation unit 104, the superpixel calculation unit 204, or the superpixel calculation unit 304 (hereinafter, simply referred to as a superpixel calculation unit) then performs registration between the ultrasound image, the CT image, and the MR image, based on the plurality of superpixels generated by the image segmentation unit, and on the label assigned in the ultrasound image. For example, first, the superpixel calculation unit determines a superpixel corresponding to the superpixel to which the label is assigned in the ultrasound image, in the CT image. The superpixel calculation unit then performs registration between the ultrasound image and the CT image, based on the superpixel to which the label is assigned in the ultrasound image, and on the superpixel determined in the CT image. The superpixel calculation unit also determines a superpixel corresponding to the superpixel to which the label is assigned in the ultrasound image, in the MR image. The superpixel calculation unit then performs registration between the ultrasound image and the MR image, based on the superpixel to which the label is assigned in the ultrasound image, and on the superpixel determined in the MR image. By performing the registration between the ultrasound image and the CT image and the registration between the ultrasound image and the MR image, registration between the CT image and the MR image is also achieved.

Further, explained in in the above embodiment is an example in which the labeling unit assigns a label to a tubular structure of a subject included in at least one of the pieces of medical image data by receiving an input operation from an operator. However, the embodiment is not limited thereto, and the labeling unit may also be configured to perform the label assignment automatically.

For example, in the registration between the ultrasound image and the CT image, the labeling unit assigns a label to the ultrasound image. Here, the labeling unit may assign the label by receiving an input operation from the operator, or automatically. To explain one example, the labeling unit extracts an end of the blood vessel represented in the ultrasound image by running a pattern matching on the ultrasound image, and assigns a label to the superpixel positioned at the extracted end. The superpixel calculation unit then performs registration between the ultrasound image and the CT image based on the label automatically assigned to the ultrasound image.

Further, explained in the above embodiments is an example in which a label is assigned to a superpixel after the superpixels are generated. However, the order of the superpixel generation and the label assignment may be any order. For example, the superpixel generation and the label assignment may be performed in parallel. It is also possible to generate superpixels after the label is assigned to the medical image data.

Further, when the label assignment is to be performed first, the superpixel generation may be performed based on the assigned label. For example, in the registration between the ultrasound image and the CT image, first, the labeling unit assigns a label to the ultrasound image by receiving an input operation from the operator, or automatically. In other words, the labeling unit assigns a label to the ultrasound image prior to the superpixel segmentation. For example, the labeling unit assigns a line drawn on the ultrasound image as a label.

The image segmentation unit then performs a superpixel segmentation on the ultrasound image based on the assigned label. For example, first, the image segmentation unit generates a small region having its centroid on the line drawn in the ultrasound image, and consisting of a group of adjacent pixels having similar image features, as a superpixel. The image segmentation unit then segments the entire ultrasound image into superpixels, by sequentially generating a small region adjacent to the generated superpixel, and consisting of a group of adjacent pixels having similar image features, as a superpixel. The image segmentation unit also determines a plurality of small blocks in the CT image based on the image features, and generates a plurality of superpixels corresponding to the determined plurality of small blocks. The superpixel calculation unit then performs registration between the ultrasound image and the CT image, based on the plurality of superpixels generated for the ultrasound image and the CT image, and on the label assigned to the ultrasound image.

Further, explained in the embodiments described above is an example in which the registration is performed by a medical image diagnostic apparatus, such as the medical image diagnostic apparatus 100, the medical image diagnostic apparatus 200, and the medical image diagnostic apparatus 300. However, the embodiment is not limited thereto.

Figure 13:
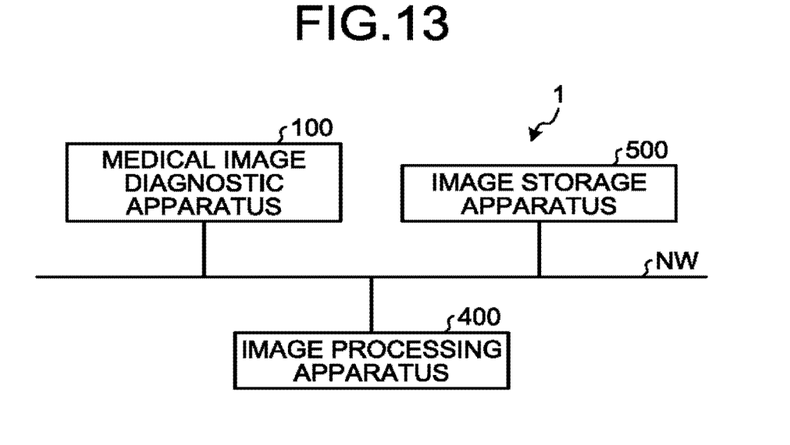
FIG. 13 is a block diagram of the exemplary structure of a medical image diagnostic system according to a fourth embodiment.

For example, the medical image diagnostic apparatus 100 may be included in a medical image diagnostic system 1 shown in FIG. 13, and an image processing apparatus 400 connected to the medical image diagnostic apparatus 100 via a network NW may perform the registration. FIG. 13 is a block diagram of an exemplary structure of a medical image diagnostic system 1 according to a fourth embodiment. The image processing apparatus 400 is implemented as a computer device such as a workstation, for example.

FIG. 13 shows an example in which the image processing apparatus 400 is connected to the medical image diagnostic apparatus 100, but the image processing apparatus 400 may be connected to the medical image diagnostic apparatus 200 or to the medical image diagnostic apparatus 300, instead of the medical image diagnostic apparatus 100. Further, although one medical image diagnostic apparatus is shown in FIG. 13, it is also possible for the medical image diagnostic system 1 to include a plurality of medical image diagnostic apparatuses.

For example, the image processing apparatus 400 has functions corresponding to those of the feature extraction unit, the image segmentation unit, the labeling unit, and the superpixel calculation unit described above, and performs registration between a plurality of pieces of medical image data. To explain one example, the image processing apparatus 400 obtains a CT image from a medical image diagnostic apparatus that is a CT scanner, and obtains an ultrasound image from a medical image diagnostic apparatus that is an ultrasonic scanner, over the network NW.

Alternatively, the image processing apparatus 400 may acquire the medical image data from an image storage apparatus 500 over the network NW. For example, the image storage apparatus 500 stores therein a CT image acquired from a medical image diagnostic apparatus that is a CT scanner, or stores the CT image in a memory provided external to the apparatus. The image storage apparatus 500 also stores therein an ultrasound image acquired from a medical image diagnostic apparatus that is an ultrasonic scanner, or stores the ultrasound image in a memory provided external to the apparatus. The image processing apparatus 400 then obtains the CT image and the ultrasound image from the image storage apparatus 500 over the network NW. The image storage apparatus 500 is implemented as a computer device such as a server device, for example.

The image processing apparatus 400 then determines a plurality of small blocks for each of the ultrasound image and the CT image, and generates a plurality of superpixels corresponding to the determined plurality of small blocks. The image processing apparatus 400 also assigns a label to at least one of the ultrasound image and the CT image. The image processing apparatus 400 then performs registration between the ultrasound image and the CT image based on the generated plurality of superpixels, and on the label assigned to the at least one of the ultrasound image and the CT image.

Further, explained in the above embodiments is an example in which the registration is performed by finding a tubular structure such as a blood vessel in a plurality of pieces of medical image data, but the region to be used in the registration is not limited to a tubular structure. In other words, the above embodiments may be applied in the same manner even when the registration is performed by finding another region such a bone or a soft tissue of the subject.

Further, the registration method explained in the first to the fourth embodiment may be implemented by causing a computer, such as a personal computer or a work station, to execute a processing program prepared in advance. This processing program may be provided over a network such as the Internet. Further, this processing program may be recorded in a computer-readable non-transitory recording medium such as a hard disk, a flexible disk (FD), a compact disc read-only memory (CD-ROM), a magneto-optical (MO) disc, or a digital versatile disc (DVD), and executed by causing a computer to read the processing program from the recording medium.

According to at least one of the embodiments explained above, it is possible to find the same corresponding structure easily in a plurality of images taken of the same patient by a plurality of imaging approaches, and to achieve registration between images of different modalities, thereby enabling rapid and accurate diagnosis.

As described above, the embodiments have been described by way of example only, and are not intended to limit the scope of the invention. The present invention can be implemented in various other forms, and various omissions, substitutions and changes can be made without departing from the spirit of the invention. These embodiments and their modifications are included in the scope and spirit of the invention, and are included in the invention recited in the technical solution and the scope of its equivalents.

What is claimed is:

1. A registration method comprising:
    determining a plurality of small blocks for each of a plurality of pieces of medical image data, and generating a plurality of superpixels corresponding to the plurality of small blocks;
    assigning a label to at least one of the plurality of pieces of medical image data; and
    performing registration between the plurality of pieces of medical image data, using the plurality of superpixels and the label.

2. The registration method according to claim 1, further comprising assigning the label to at least one of the superpixels in at least one of the plurality of pieces of medical image data.

3. The registration method according to claim 1, further comprising determining a plurality of small blocks based on the label, for the piece of medical image data to which the label is assigned, among the plurality of pieces of medical image data, and generating a plurality of superpixels corresponding to the plurality of small blocks.

4. The registration method according to claim 1, further comprising assigning the label to at least one of the plurality of pieces of medical image data by receiving an input operation from an operator.

5. The registration method according to claim 1, wherein the plurality of pieces of medical image data include first image data and second image data, further comprising:
    generating a plurality of superpixels for each of the first image data and the second image data;
    assigning the label at least to the first image data;
    determining a second superpixel in the second image data, the second superpixel being a superpixel corresponding to a first superpixel to which the label is assigned in the first image data; and
    performing registration between the first image data and the second image data based on the first superpixel and the second superpixel.

6. The registration method according to claim 1, further comprising receiving a correction indication issued by an operator via assignment of the label, in response to a result of the registration; and
    regenerating a superpixel based on the label assigned as the received correction indication.

7. The registration method according to claim 1, further comprising assigning the label to a region of a subject included in at least one of the plurality of pieces of medical image data.

8. The registration method according to claim 6, further comprising learning the received correction indication, and to reflect a result of the learning to a subsequent generation of the superpixels.

9. The registration method according to claim 7, wherein the region is a tubular structure.

10. The registration method according to claim 7, further comprising
    calculating a centroid of a superpixel as a center point of the superpixel;
    generating a transformation matrix between a first region in first image data and a second region in second image data, in accordance with coordinates of center points of at least two superpixels of the first region, and with coordinates of center points of corresponding superpixels of the second region, the corresponding superpixels being superpixels corresponding to the at least two superpixels;
    generating predicted coordinates of a center point of a second superpixel of the second region, the second superpixel being a superpixel corresponding to a first superpixel of the first region, in accordance with coordinates of a center point of the first superpixel and the transformation matrix;
    selecting a plurality of superpixels within a range of a predetermined radius centered on the predicted coordinates;
    calculating a similarity between a feature of the first superpixel of the first region and a feature of each of the plurality of superpixels selected within the range of the predetermined radius centered on the predicted coordinates; and
    determining a superpixel exhibiting a most similar feature in the second region, as the second superpixel, among the plurality of superpixels selected within the range of the predetermined radius centered on the predicted coordinates.

11. The registration method according to claim 9, wherein the tubular structure is a blood vessel.

* * * * *